(12) United States Patent
Kerr

(10) Patent No.: US 8,231,605 B2
(45) Date of Patent: Jul. 31, 2012

(54) DIALYSIS CATHETER

(76) Inventor: Andrew Kerr, New York, NY (US)

( * ) Notice: Subject to any disclaimer, the term of this patent is extended or adjusted under 35 U.S.C. 154(b) by 0 days.

(21) Appl. No.: 12/611,959

(22) Filed: Nov. 4, 2009

(65) Prior Publication Data

US 2010/0049116 A1 Feb. 25, 2010

Related U.S. Application Data

(60) Division of application No. 11/972,045, filed on Jan. 10, 2008, now abandoned, which is a continuation-in-part of application No. 11/807,575, filed on May 29, 2007, now abandoned, which is a division of application No. 11/287,789, filed on Nov. 28, 2005, now Pat. No. 7,258,685.

(60) Provisional application No. 60/631,473, filed on Nov. 29, 2004.

(51) Int. Cl.
*A61M 25/16* (2006.01)

(52) U.S. Cl. ........................................ 604/539

(58) Field of Classification Search ............... 604/93.01, 604/539, 164.04, 253, 533, 171, 175, 264
See application file for complete search history.

(56) References Cited

U.S. PATENT DOCUMENTS

| | | | |
|---|---|---|---|
| 5,341,816 A * | 8/1994 | Allen | 600/567 |
| 6,361,541 B1 * | 3/2002 | Barnhart | 606/108 |
| 2007/0185510 A1 | 8/2007 | Tran | |

* cited by examiner

*Primary Examiner* — Christopher D Koharski
(74) *Attorney, Agent, or Firm* — Gerald E. Hespos; Michael J. Porco

(57) ABSTRACT

A catheter assembly includes catheter having proximal and distal ends and at least one lumen extending between the ends. At least one end of the catheter is formed from a material that can be trimmed to achieve a selected length for the catheter. A tubular connector is telescoped over the catheter and a hub is joined to the tubular connector. Proximal portions of the hub are configured for connection to a medical apparatus. A cuff is mounted around the tubular connector or the catheter. The cuff is formed from a material that will permit or promote the growth of scar tissue for anchoring the catheter device at least on a semi-permanent basis in a patient.

3 Claims, 14 Drawing Sheets

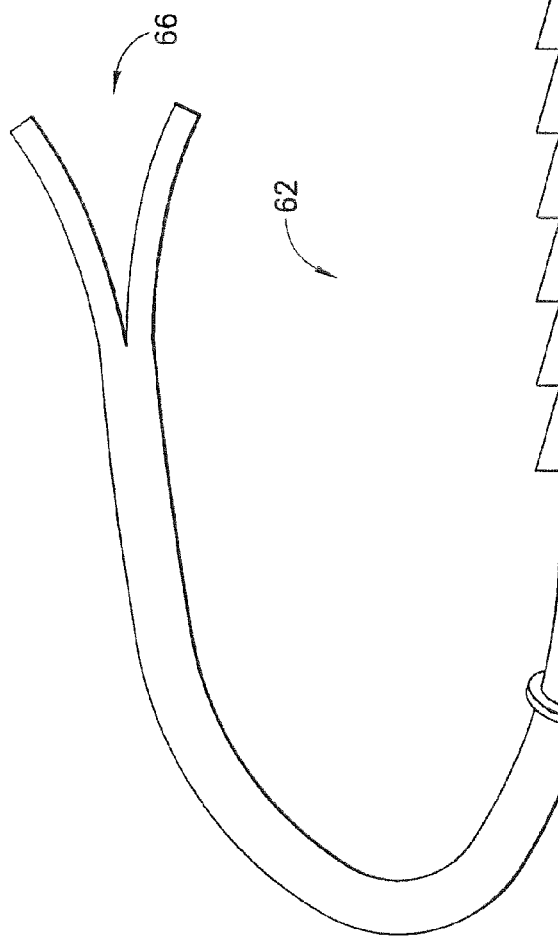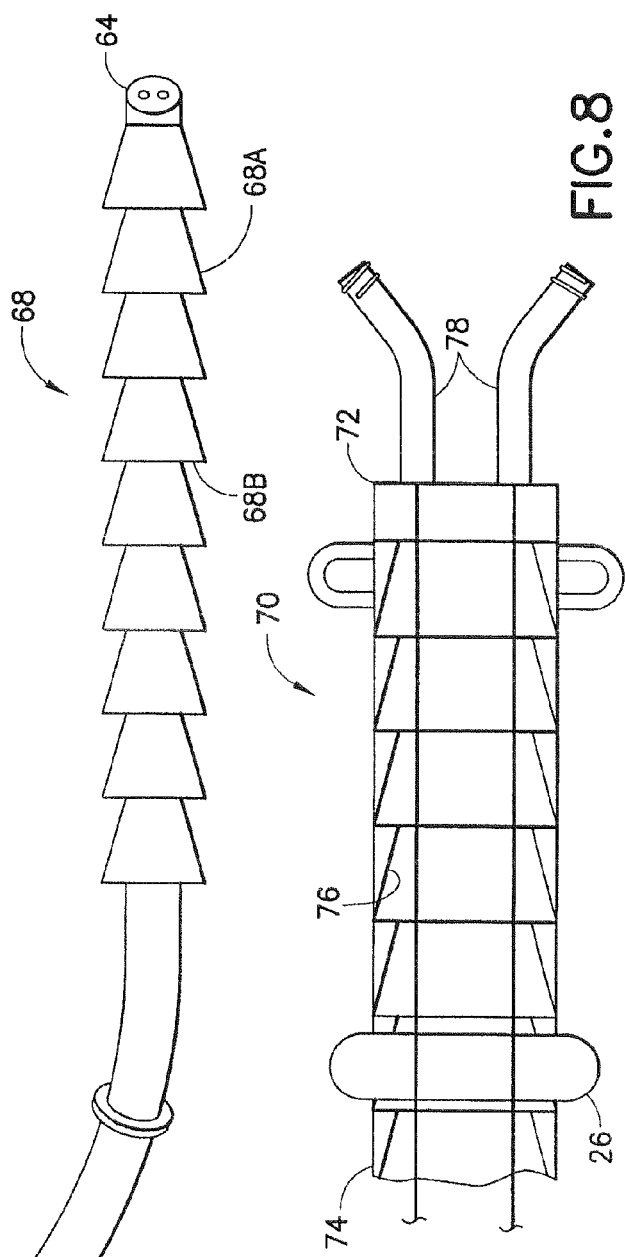

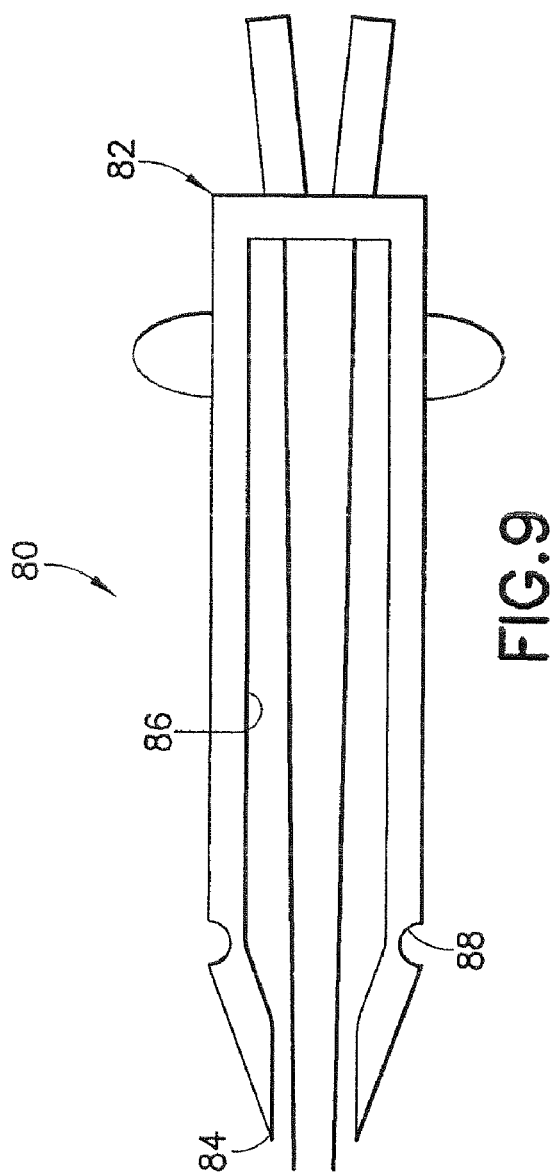
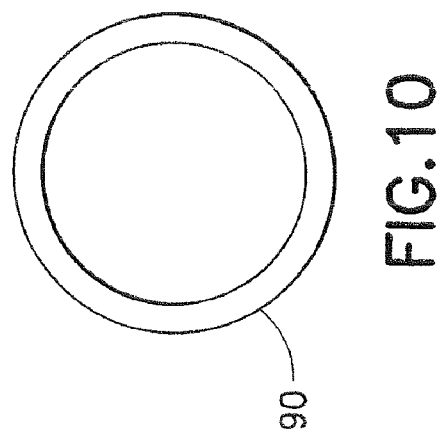

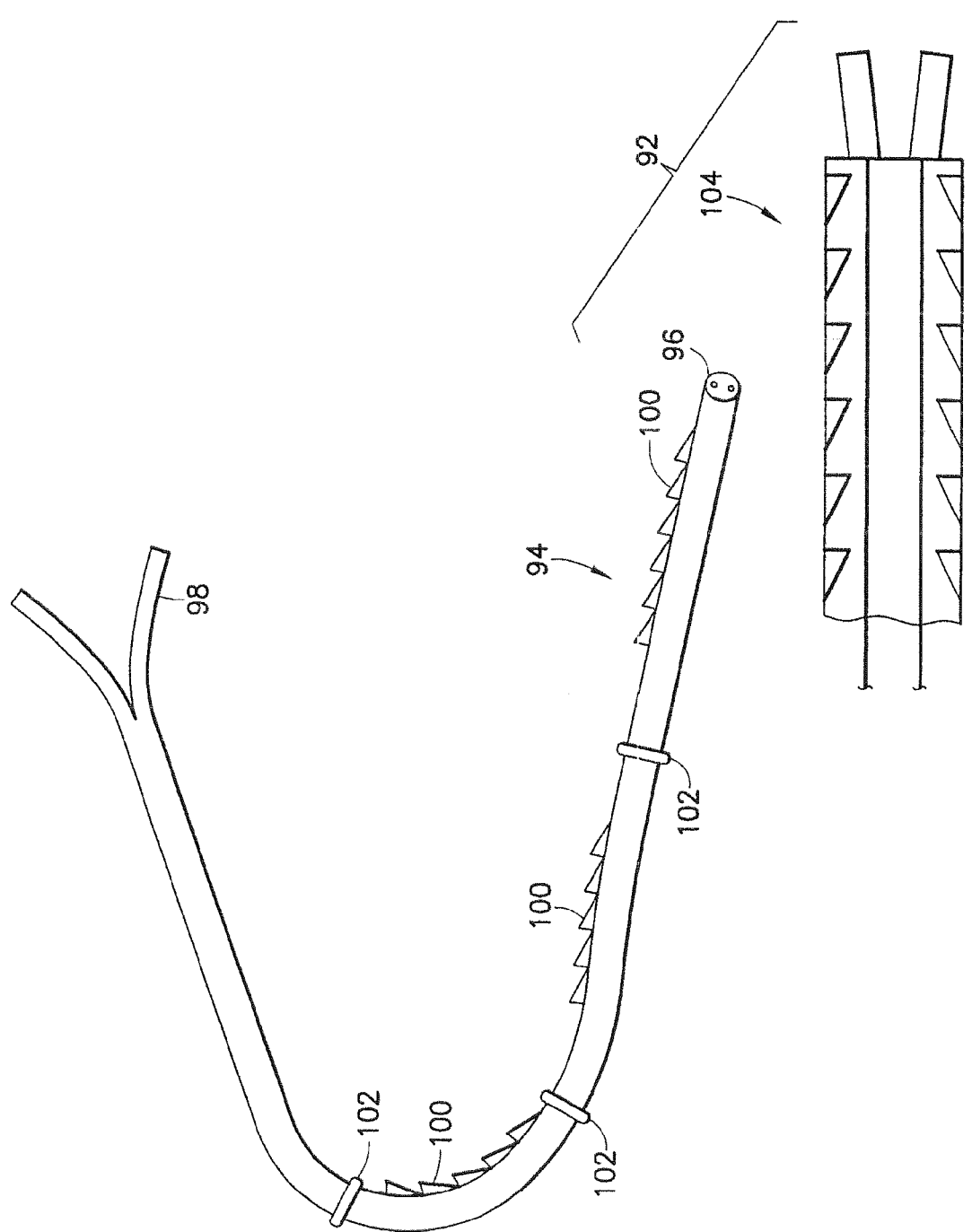

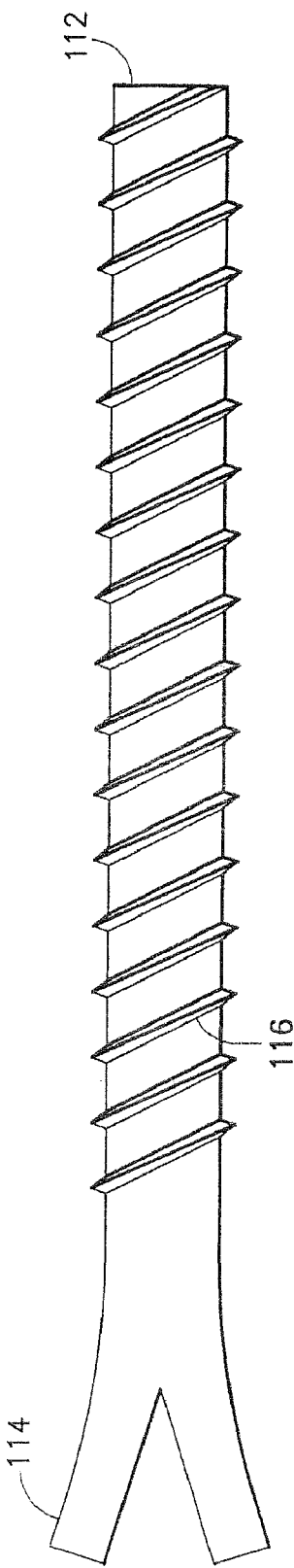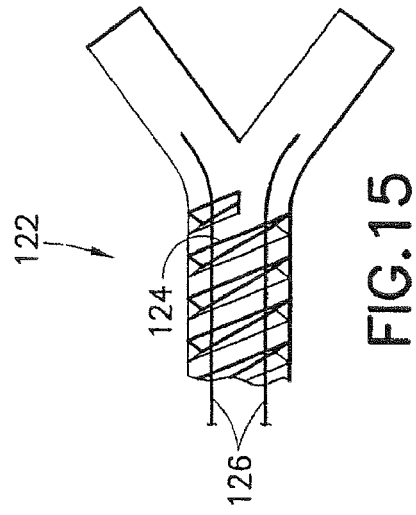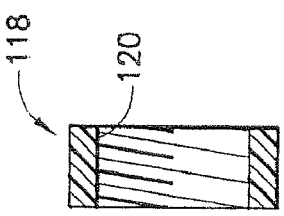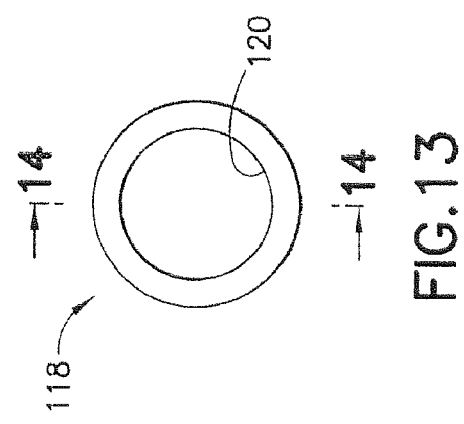

METAL CANNULAS

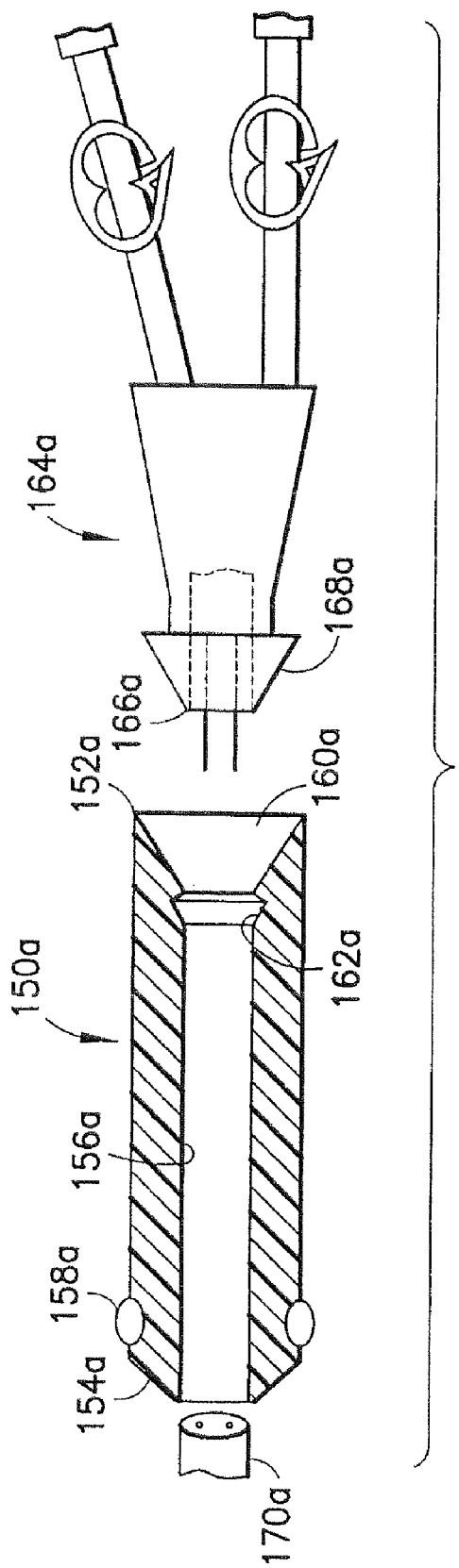
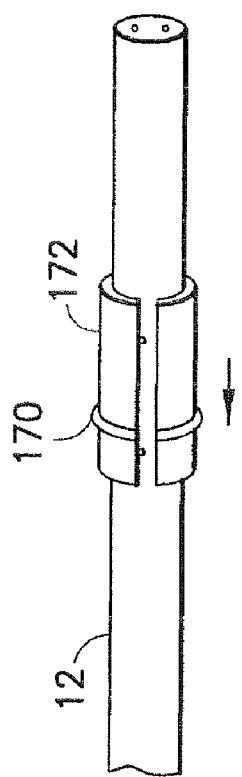

DIALYSIS CATHETER

This application is a divisional of U.S. patent application Ser. No. 11/972,045, filed on Jan. 10, 2008, which is a continuation-in-part of U.S. patent application Ser. No. 11/807,575, which in turn is a divisional of U.S. patent application Ser. No. 11/287,789 now U.S. Pat. No. 7,258,685, and which claimed the benefit of Application No. 60/631,473 filed Nov. 29, 2004.

BACKGROUND OF THE INVENTION

1. Field of the Invention

The invention relates to a catheter that can be used for dialysis or for other procedures where the catheter is implanted for an extended period of time.

2. Description of the Related Art

Dialysis and some chemotherapy regimens require a catheter to be implanted in a patient for an extended time (e.g., several weeks, several months or longer). Catheters for dialysis extend from an externally accessible location on the patient (typically on the chest) to a location where there is a high flow of blood (typically near the heart). The high blood flow enables a sufficient volume of blood to be processed through the catheter and cleaned by the dialysis machine. Catheters used for chemotherapy and other drug administration purposes are extended from an externally accessible location on the patient to a location where the drug is likely to be most effective. The following discussion will pertain mostly to catheters intended for dialysis. However, the subject invention is applicable to all catheters that are implanted for an extended time.

A discussion of catheters is provided in *Venous Catheters A Practical Manual* by Pieters et al. Chapter 4 of that work is entitled *Central Venous Catheters: Materials, Designs and Selection* by Matthew A. Mauro, and the disclosure of that Chapter 4 is incorporated herein by reference.

Briefly, the distal end of a dialysis catheter should be placed close to the heart for optimum exchange of blood. Doctors typically want to know the location of the distal end of the dialysis catheter with considerable precision. The proximal end of the dialysis catheter desirably is at a location that can be accessed conveniently during dialysis and that is unobtrusive between the periodic dialysis procedures. Many doctors choose to direct the dialysis catheter through the jugular vein. However, the neck certainly is not the unobtrusive location for keeping the proximal end of the dialysis catheter between the periodic dialysis procedures.

The dialysis catheter typically is formed from a flexible material, such as silicone. A typical medical procedure for implanting a dialysis catheter involves first placing a small incision in the skin of the neck over the jugular vein. Subsequently, the jugular vein is cannulated. A peelable introducer sheath then is advanced an appropriate distance into the blood vessel so that the end of the catheter is at the precise position preferred by the doctor. The doctor then employs a tunnel dilator to create a subcutaneous tunnel that permits the proximal end of the catheter to be at a less obtrusive position. The subcutaneous tunnel typically extends slightly below the skin from a location on the chest and under the clavicle to a location where the catheter has been introduced into the jugular. The doctor directs the catheter through the tunnel, to the neck, through the incision in the neck and through the introducer sheath. The introducer sheath then is removed. A hub at the proximal end of the catheter may include a Luer fitting that enables the proximal end of the catheter to be placed in communication with the dialysis machine. Several closure means are provided on or near the proximal end of the catheter to prevent unintended blood loss between the periodic dialysis procedures.

Blood pressure and other forces within the body tend to urge the catheter from the body. Hence, proper anchoring is important. One common anchoring means provides a cuff extending around the portion of the catheter in the tunnel that extends from the upper chest to the neck of the patient. The cuff typically is formed from polyester. Scar tissue accumulates around the cuff and functions to hold the catheter in place. The scar tissue may also function as a barrier to bacterial infection. The scar tissue results in at least a semi-permanent anchoring of the catheter. In this regard, semi-permanent means that the catheter will remain in the patient until the cuffed portion of the catheter is dissected from the patient. This dissection can be complicated.

Dialysis catheters vary considerably from one manufacturer to another. However, a common requirement for virtually all dialysis catheters is an ability to locate the distal end of the catheter and the cuff with considerable precision. Accordingly, the doctor has limitations on the distance between the distal tip of the catheter and the cuff depending upon physical characteristics of the patient. A smaller patient will require a smaller tip-to-cuff distance, while a larger patient will require a larger tip-to-cuff distance. In view of these physical differences between patients, most dialysis catheter manufacturers provide catheters with different tip-to-cuff length. Accordingly, hospitals must maintain an appropriate inventory of different length dialysis catheters and the doctor must ensure that a catheter of appropriate length is available for implementation. There are costs and complications associated with a need to maintain an inventory of different products.

Compromises often must be made when a doctor selects a dialysis catheter from an inventory of catheters with different lengths. In this regard, dialysis catheters often come with tip-to-cuff lengths of 19 cm, 23 cm, 28 cm and 32 cm. A selection of a catheter of one of these lengths may require the doctor to move the tip or the cuff from its optimal position.

Arrow Cannon markets a dialysis catheter with most of the features described above. The Arrow Cannon catheter is promoted as having an ability to assure accurate tip placement. In this regard, the tip of the catheter is placed in the jugular in the manner described above. Proximal portions of the catheter then are urged in a retrograde direction through the tunnel from the neck to the selected location on the chest. The portion of the catheter emerging from the chest then is cut. A compression cap and compression sleeve are mounted separately to the cut proximal end of the catheter and a hub is threadedly engaged with the compression cap. The above-described Arrow Cannon catheter has the above-described problems associated with inventory management. Additionally, even though the tip may be positioned accurately, the cuff location is dependent upon the different tip-to-cuff dimensions in the inventory. Additionally, the retrograde movement of the catheter through the tunnel requires a technique that many doctors are not accustomed to. Furthermore, the intraoperative assembly of the compression sleeve with the compression cap requires more procedural steps and takes additional time.

U.S. Pat. No. 5,989,213 relates to a dialysis catheter with a guide tube that fits into the blood vessel. A tissue ingrowth member is secured to proximal portions of the guide catheter for affixation to the subcutaneous tissue. Thus, distal portions of the guide catheter of U.S. Pat. No. 5,989,213 reside in the blood vessel and proximal portions of the guide catheter are secured to the subcutaneous tissue. The dialysis catheter then is passed through the guide catheter. The distal end of the dialysis catheter is disposed at an appropriate location in the circulatory system, and distally of the distal end of the guide catheter. Proximal ends of the dialysis catheter are disposed externally on the patient, and proximally of the proximal end of the guide catheter. The system shown in U.S. Pat. No. 5,989,213 permits a desired distance between the distal tip of the catheter and the tissue ingrowth cuff. However, the system shown in U.S. Pat. No. 5,989,213 is not trimmable and hence requires an extensive inventory of catheters of different length to ensure that an excess of the catheter is not disposed externally of the patient.

Accordingly, it is an object of the subject invention to provide an improved catheter that can be implanted for an extended time, such as a dialysis catheter.

Another object of the subject invention is to provide a catheter that substantially avoids the need to maintain a significant inventory, while permitting precise positioning of both the tip and the cuff.

A further object of the invention is to provide a catheter that is convenient to implant and that ensures a precise exit site on the chest for the catheter.

SUMMARY OF THE INVENTION

The subject invention is directed to a catheter assembly. The assembly includes a catheter with a proximal end, a distal end and at least one lumen extending therethrough. Catheters intended for use with a dialysis apparatus preferably include at least two lumens extending between the proximal and distal ends. In this context, the distal end of the catheter is considered to be the end that is positioned at an appropriate location in the patient, such as in a major blood vessel near the heart. The proximal end of the catheter is considered the end disposed externally of the patient and near the doctor who is performing the implantation. At least the proximal parts of the catheter are formed from a material that is easily trimmable.

The catheter assembly further includes a means for promoting growth of tissue for fixing the catheter at a selected location relative to a subcutaneous tunnel formed for implantation of the catheter. The means for promoting growth of tissue may be formed from or treated with a fibrosing agent. Fibrosing agents include, but are not limited to silk, collagen, talc, talcum powder, beryllium, copper, silica, quartz, EVA, PLA, polyurethane and polymerized drug compositions. Preferably the means for promoting growth of tissue comprises a cuff mounted around or near the catheter either intraoperatively or immediately prior to implantation. The cuff preferably has a first orientation where the cuff is movable relative to the catheter and a second orientation where the cuff is fixed relative to the catheter. For example, the cuff initially may be a substantially linear structure with opposite first and second ends. The cuff is deformable or deflectable from the initial linear condition into an annular condition. Additionally, the opposed ends of the cuff are securely connectable to one another so that the cuff can be secured around the catheter. The dimensions of the cuff are selected to ensure secure mounting of the cuff around the catheter without constricting the flow of fluid through the catheter. The structure for locking the opposite ends of the cuff together may include interengageable teeth such as the interengagement employed on a wire wrap. Alternatively, the opposed ends of the cuff can have a projection and an aperture respectively that engage much in the manner of a dovetail connection. The connection and mounting of the cuff may be similar to the connection and mounting of band clamps, hose clamps, tube clamps, J-type clamps, one-ear clamps, two-ear clamps and other clamps that secure a flexible member around the outer circumference of a cylindrical member. Such connectors are shown in the MSC Industrial Supply Co. catalog, the disclosure of which is incorporated herein by reference.

The cuff may be engaged directly on the catheter. However, a preferred embodiment includes a subcutaneous tube that is telescoped over the proximal end of the catheter, and the cuff is engaged around portions of the subcutaneous tube that are telescoped over the proximal end of the catheter. The proximal end of the catheter and the subcutaneous tube may have smooth tubular surfaces that telescope into engagement with one another. The assembly may then include a compression cap and a compression sleeve. A Luer hub can be threaded into engagement with the compression cap to deform the compression sleeve sufficiently for interengagement with the catheter and the subcutaneous tube. The compression sleeve preferably is pre-assembled with the compression cap in a manner that substantially prevents axial movement between the compression sleeve and the compression cap while permitting the compression sleeve to rotate relative to both the catheter and the compression cap. Hence, the doctor is not required to assemble the compression sleeve with the compression cap intraoperatively or immediately prior to implementation. Additionally, the ability of the compression sleeve to rotate relative to the compression cap and the catheter prevents the creation of a torque that could twist and constrict or damage the catheter. Various other optional connections between the catheter and the subcutaneous tube may be similar to couplings in the above-referenced MSC Industrial Supply Co. catalog, the disclosure of which is incorporated herein by reference.

An alternate version of the catheter assembly may include may include a cuff tube with a proximal end, a distal end and a lumen extending between the ends. The lumen is configured so that the cuff tube can be telescoped over proximal portions of the catheter. The above described cuff may be mounted to an appropriate location on the outer periphery of the cuff tube. In this regard, the cuff tube can be formed with surface configurations on the outer periphery for positioning and holding the cuff. In other embodiments, the cuff may be premounted to a selected location on the cuff tube. The premounting of the cuff on the cuff tube can be achieved, for example, by adhesive. The cuff tube further may include a hub mounting structure at a location on the outer periphery near the proximal end. Additionally, the cuff tube may include means for constricting portions of the cuff tube into a secure mechanical and fluid tight engagement with the catheter. The hub of this embodiment is configured for secure mounting over proximal portions of the cuff tube. The mounting may be achieved by a snapped engagement of the hub mounting structure on the cuff tube with corresponding structure on the hub. The assembly of this embodiment is employed by initially positioning the catheter as described above. The cuff tube then is slid over proximal portions of the catheter and the attachments means near proximal portion of the cuff tube are tightened to achieve secure engagement of the cuff tube with the catheter. Portions of the catheter that extend proximally beyond the cuff tube then are trimmed. The hub then is mounted over and secured to the cuff tube. The hub can be configured to mount over or into proximal portions of the cuff tube. Additionally, engageable regions of cuff tube and the hub can be configured to compress the cuff tube or the hub inwardly to achieve a secure mechanical and fluid tight interconnection between the cuff tube, the catheter and the hub. This embodiment can avoid the need for a separate attachments means to secure the cuff tube to the catheter.

Another preferred embodiment of the invention provides a catheter with a proximal end configured with a plurality of undulations. Each undulation may include a conically sloped proximal face and a radially aligned distal face. The catheter may be employed with a hub having an inner tubular surface with internal undulations configured for mating with the outer surface configuration on the proximal end of the catheter. The conical and radial surfaces on the undulations on the catheter and the hub are oriented and configured so that the catheter and the hub can be telescoped together easily (i.e., engagement of the conical surfaces), but cannot be separated (i.e., engagement of the radial surfaces). The above-described cuff can be mounted around either a portion of the catheter or a portion of the hub. The hub may include a notch for affixing the cuff at a fixed axial position on the hub.

In an alternate embodiment, the proximal end of the catheter can be formed with an array of external threads and the interior of the hub can be formed with an array of internal threads that can be mated with the threads on the catheter. The cuff can be the above-described cuff that initially is substantially linear and that is mounted subsequently around the catheter or the hub. Alternatively, the cuff can be provided with its own internal array of threads for mounting over the proximal end of the catheter or over the hub.

The hub can include an array of external threads and a cap or nut can be threaded over the hub. In this embodiment, the proximal end of the catheter can merely be inserted axially into the hub. The cap or nut then is rotated about the hub and is configured to compress the hub into engagement with the proximal end of the catheter. In this embodiment, the cap or nut preferably includes known structure for permitting rotation in one direction while preventing or complicating rotation in the opposed direction so that the cap or nut will not dislodge unintentionally. For example, the threads on the cap and the hub may be configured to deform and substantially lock as the cap or nut is rotated. Alternatively, a biased arrangement that requires both axial and rotational movement can be provided in much the same manner as the arrangements provided on a childproof medicine bottle.

A further embodiment of the subject catheter assembly may include a dual lumen catheter with opposite proximal and distal ends defining a length sufficient to conform to the maximum anticipated length of the required catheter for all patients. A cuff is mounted fixedly and permanently to the catheter near the proximal end. The distal end of the catheter then may be trimmed to the specific required length. One of the two lumens then is cut to a shorter length than the other. If necessary or desired, the two different length lumens may be separated slightly from one another near the distal end. Thus, a catheter of the precise appropriate length is assured. Additionally, the distal ends of the lumen are positioned properly relative to one another to ensure a good flow of blood to and from the dialysis machine, and to ensure that the recently cleaned blood is not recirculated back directly into the dialysis machine.

In certain embodiments, the cuff can be a continuous ring that is slid over the catheter after the distal tip of the catheter has been positioned properly in the patient, but before the proximal portions of the catheter are advanced through the tunnel. In this regard, the assembly may include a longitudinally slit tube that can be mounted over a proximal portions of the catheter. This slit tube then can be employed to advance the cuff distally to a proper position. The opposed longitudinal edges of the slit tube then can be secured together for properly holding the slit cylindrical tube to the catheter and for properly positioning the cuff on the catheter. Inner circumferential surfaces of the slit tube may include a layer of resilient material to assure a liquid tight seal against the catheter.

As noted above, a patient eventually may reach a point where further dialysis is unnecessary. However, the scar tissue that intentionally is developed around the cuff can complicate efforts to remove the cuff and specifically requires significant dissection. The catheter assembly of the subject invention can be used with a cuff removal tool. The cuff removal tool may include a short cylindrical tube with proximal and distal ends. The distal end of the tube may be formed with an array of distally directed teeth. The proximal end of the tube may include a handle to facilitate gripping and rotation of the tube. The tube may be a slit cylinder that can be closed into a complete cylinder. The cylindrical tube is in its open condition for mounting on the catheter or hub. The tube then can be urged into its closed position. Rotation of the cylindrical tube will cause the teeth at the distal end of the tube to cut through the scar tissue around the cuff so that the catheter can be removed with relative ease. This tube can be use with any of the above described embodiments of the catheter assembly as well as with prior art catheters.

The catheter assembly of the subject invention has several advantages over known structures and assemblies. In particular, there is no need to keep an inventory of catheters of various lengths. Catheters of the maximum optional length can be provided with all assemblies and can be trimmed immediately preoperatively or intraoperatively to the precise required length.

Catheters can become blocked or infected. Most prior art devices require surgical removal of the cuff to replace the blocked or infected catheter. However, the assembly of the subject invention permits replacement of the catheter without dissecting the biologically secured cuff from the patient. In this regard, the compression cap or other attachment means can be disengaged so that the catheter can be separated and replaced without affecting the securely mounted cuff.

The catheter assembly of the subject invention also provides the operator with complete control of the catheter tip and the tunnel exit site positions. This distinguishes from prior art devices where compromises may have to be made on either the location of the tip or the exit site depending upon the length of the catheter chosen by the doctor.

As noted above, most doctors prefer the more common antegrade movement of the catheter through the tunnel. However, doctors familiar with the Arrow Cannon devices may have acquired familiarly with a retrograde movement of the catheter through the subcutaneous tunnel. The catheter assembly of the subject invention permits both antegrade or retrograde tunneling techniques, and hence permits doctors to employ the technique with which they have become most familiar.

Many patients eventually will reach a point where the catheter is no longer needed. Removal of the prior art catheter can be complicated in some prior art devices depending upon the positioning of the proximal end of the catheter. However, the proximal end of the catheter of the subject assembly is always reliably near the subcutaneous tunnel exit, and hence can be accessed easily for removal of the catheter.

As noted above, a dialysis catheter is intentionally in communication with a high volume blood vessel. Accordingly, bleeding from the tunnel exit site remains a potential problem. However, the hub extension of the subject invention is configured to prevent bleeding from the tunnel exit site. Additionally, the hub extension provides an additional layer of protection for the catheter against ascending bacteria.

A further variation of the invention includes a catheter, as described above, an outer subcutaneous tube, a cap, a hub and an inner subcutaneous tube. The outer subcutaneous tube and the cap each have opposite proximal and distal ends and a lumen extending between the ends. The proximal end of the outer subcutaneous tube is connected permanently to the cap so that the lumen through the outer subcutaneous tube communicates with the lumen through the cap. Thus, the outer subcutaneous tube and the cap define an integral subassembly. Portions of the outer subcutaneous tube adjacent the distal end are intended to be placed in a subcutaneous tunnel formed in the patient. Thus, a fibrous cuff or other fibrosing agent is disposed around the outer circumferential surface of the outer subcutaneous tube at locations near the distal end. The inner subcutaneous tube also has opposite proximal and distal ends and a lumen extending between the ends. The proximal end of the inner subcutaneous tube is connected permanently to the hub so that the inner subcutaneous tube and the hub define an integral subassembly. The lumen of the inner subcutaneous tube is configured for slidably receiving the catheter. Portions of the inner subcutaneous tube adjacent the distal end have an outer circumferential dimension configured to be received closely in the lumen of the outer subcutaneous tube. Additionally, the hub and the cap are configured to be connected releasably after the inner subcutaneous tube is slid through the lumen of the cap and into the lumen of the outer subcutaneous tub.

This embodiment, with the inner and outer subcutaneous tubes, can be used in a manner similar to the above-described embodiments and has all of the advantages of the above-described embodiments. In particular, the catheter can be placed in the patient in a conventional antegrade or retrograde manner so that proximal portions of the catheter extend from the patient. The proximal end of the catheter then is trimmed to an appropriate selected length. The integral subassembly of the hub and the inner subcutaneous tube is assembled loosely by the manufacturer with the integral subassembly of the outer subcutaneous tube and the cap so that distal end of the inner subcutaneous tube is in and near the distal end of the outer subcutaneous tube. The trimmed proximal end of the catheter then is telescoped into the lumen at the distal end of the inner subcutaneous tube and is advanced until the proximal end of the catheter substantially reaches the hub. The hub then is tightened relative to the cap and deforms the proximal end of the inner subcutaneous tube inwardly and into engagement with the catheter to create a fluid tight engagement.

A catheter can become infected or blocked, and in these circumstances must be exchanged. The latter embodiment permits easy replacement of the catheter without disengaging the outer subcutaneous tube that has been anchored securely in the patient by the fibrous cuff. In this regard, the subassembly of the hub and the inner subcutaneous tube can be separated from the cap and the outer subcutaneous tube and can be removed from the patient. The catheter then can be removed from the subassembly of the cap and the outer subcutaneous tube and from the patient. A new catheter then is advanced through the lumens of the cap and the outer subcutaneous tube and into the patient. A new subassembly of a hub and an inner subcutaneous tube then is placed in communication with the distal end of the catheter. The new inner subcutaneous tube is telescoped closely through the lumen of the cap and into the lumen of the outer subcutaneous tube. The hub and the cap then are tightened and squeeze the inner subcutaneous tube into engagement with the catheter. This embodiment, with the combination of inner and outer subcutaneous tubes, protects the catheter from ascending infection and is more effective at preventing bleeding at the tunnel exit site, as explained herein.

BRIEF DESCRIPTION OF THE DRAWINGS

FIG. 7 is a schematic view of a second embodiment of a catheter in accordance with the subject invention.

FIG. 8 is a schematic view of a hub for use with the catheter of FIG. 7.

FIG. 9 is a schematic view of a third embodiment of a catheter and hub assembly in accordance with the invention.

FIG. 10 is a schematic elevational view of a cuff for use with the catheter and hub of FIG. 9.

FIG. 11 is a schematic view of a fourth embodiment of a catheter and hub assembly in accordance with the subject invention.

FIG. 12 is a schematic elevational view of a fifth embodiment of a catheter in accordance with the subject invention.

FIG. 13 is a schematic view of a cuff for use with the catheter of FIG. 12.

FIG. 14 is a cross-sectional view taken along line 14-14 in FIG. 13.

FIG. 15 is a schematic elevational view of a cuff for use with the catheter of FIG. 12 and the cuff of FIG. 13.

FIG. 19 is a schematic view of a ninth embodiment where the cuff tube functions as a compression cap for compressing the hub.

FIG. 20 is a schematic view of a tenth embodiment with a slit cuff tube.

DETAILED DESCRIPTION OF THE PREFERRED EMBODIMENTS

Figure 1A:
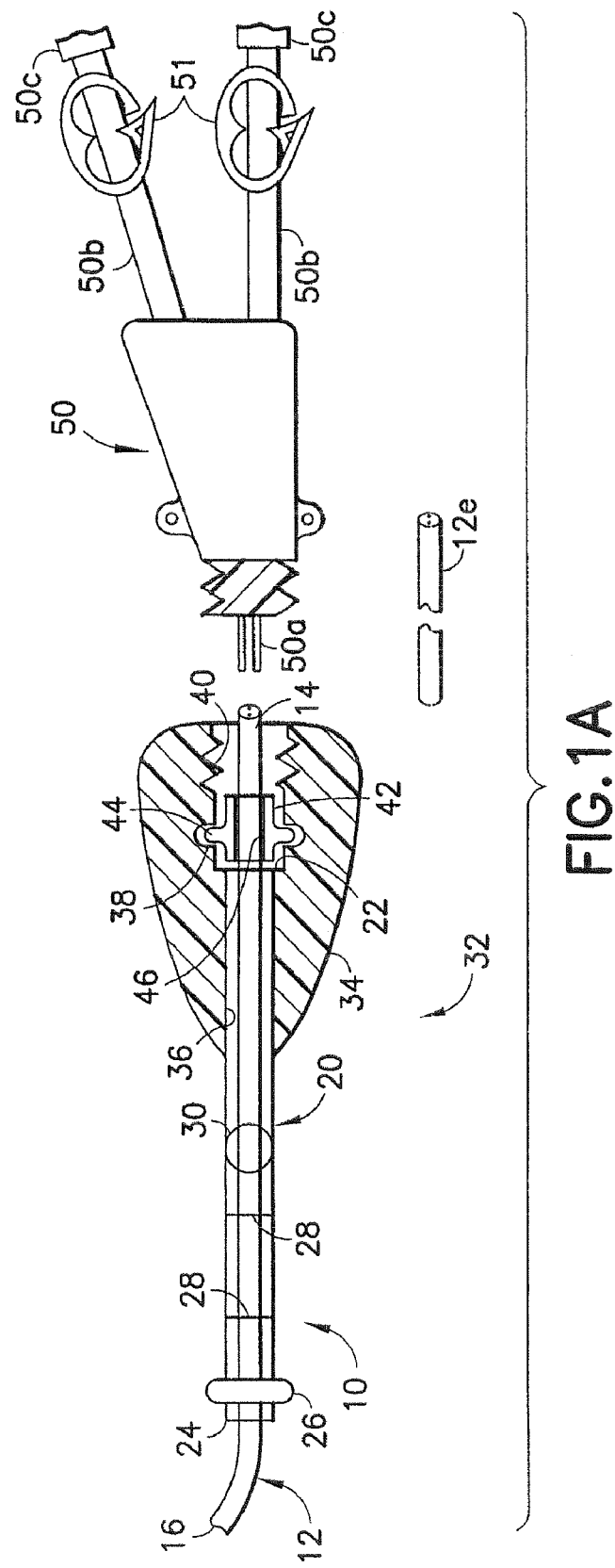
FIG. 1A is a schematic view of a first embodiment of a catheter in accordance with the subject invention.

A dialysis catheter assembly in accordance with a first embodiment of the invention is identified generally by the numeral 10 in FIG. 1A. The catheter assembly 10 includes a catheter 12 with a proximal end 14 and a distal end 16. The proximal end 14 will be disposed externally on the patient, while the distal end 16 will be positioned at a selected location in a blood vessel of the patient, and preferably in close proximity to the heart of the patient. A subcutaneous tube 20 is mounted over a portion of the catheter 12 near the proximal end 14. The subcutaneous tube 20 will be disposed in a subcutaneous tunnel extending from a location on the chest of the patient to a location near the neck of the patient. The tube 20 includes a proximal end 22 that will be disposed externally of the patient and a distal end 24 that will be in the subcutaneous tunnel. A polyester cuff 26 or other fibrosing agent is disposed near the distal end of the tube 24 and is configured to promote the growth of scar tissue that will hold a catheter assembly 10 in place in the subcutaneous tunnel in the patient. The cuff 26 preferably is permanently disposed on the tube 20 by the manufacturer, and hence requires no preoperative or intraoperative manipulation by medical personal. However, as explained herein the cuff 26 can be designed for easy mounting by the doctor. The tube 20 may further include indicia 28 to mark a depth of insertion of the tube 20 into the patient. Additionally, the tube 20 may include a substantially transparent window 30. The catheter 12 may further include indicia to mark dimensions and hence volumes from the distal end 16 of the catheter 12. The markings on the catheter 12 can be visible through the window 30 in the tube 20 disposed externally of the patient. A doctor can rely upon these visible observations to determine an appropriate volume of heparin solution that should be inserted into the assembly 10 to prevent clotting.

A compression cap assembly 32 is mounted over the proximal end 22 of the tube 20 and includes a cap 34 with a passage 36 extending therethrough. The proximal end of the passage 36 includes an annular groove 38 and an array of internal threads 40. The compression cap assembly 32 further includes a compression sleeve 42 with an annular rib 44 trapped in the annular groove 38 of the passage 36 through the cap 34. Thus, the compression sleeve 42 is rotatable in the compression cap 34, but is trapped axially. The compression sleeve 42 further includes a passage 46 dimensioned to permit the catheter 12 to be passed therethrough.

The assembly 10 further includes a hub assembly 50 that can be threaded into engagement with the internal threads 40 on the cap 34. Two cannulas 50a project from the hub assembly 50 and are dimensioned for insertion into the respective lumens in the catheter 12. Tubes 50b extend proximally from the hub assembly 50 and communicate respectively with the cannulas 50a. Luer lock fittings 50c are secured to ends of the tubes 50b remote from the housing of the hub assembly 50 and clamps 51 are mounted to the respective tubes 50b distally of the Luer lock fittings 50c. The clamps 51 are operative to selectively close the tubes 50b. Threaded engagement of the hub 50 into the cap 34 compresses the catheter 12, securely holds the catheter 12 and attaches the entire compression cap assembly 32 to the catheter 12. The catheter assembly of FIG. 1A is implanted substantially in the conventional manner described above. However, the subcutaneous tube 20 is telescoped over the proximal end of the catheter 12 and into the subcutaneous tunnel prepared by the surgeon after the catheter 12 has been positioned. The tube 20 is advance so that the distal end 24 of the tube is in a subcutaneous position in the prepared tunnel and spaced from the vein that has been accessed by the catheter 12. The surgeon then trims proximal portions of the catheter 12 near the proximal end of the compression cap assembly 32. Excess 12e of the catheter 12 then may be discarded. The cannula 50a of the hub assembly 50 then are passed into the lumens of the dialysis catheter 12 and the hub assembly 50 is threaded into engagement with the compression cap assembly 32. As a result, the surgeon is assured of having a precise desired tip to cuff length and a desired precise positioning of both the proximal and distal ends 14 and 16 of the catheter 12.

Figure 1B:
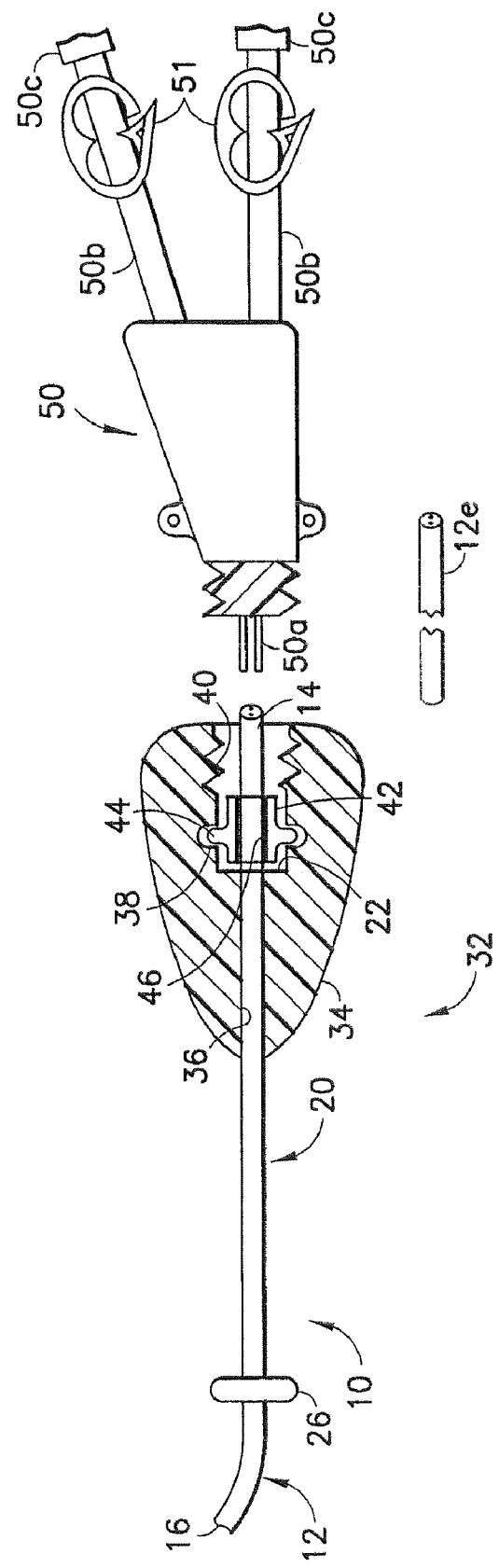
FIG. 1B is a variation of the embodiment of the FIG. 1A.

FIG. 1B shows an alternate dialysis catheter assembly that is identified generally by the numeral 10B. The assembly 10B is very similar to the dialysis catheter assembly 10 described above and illustrated in FIG. 1A. However, the dialysis catheter assembly 10B has no equivalent to the subcutaneous tube 20. As a result, the polyester cuff 26 or other fibrosing agent is mounted directly on the catheter 12. Additionally, the compression cap assembly 32 is mounted directly on the catheter 12. With this FIG. 1B design option, the polyester cuff 26 cannot be mounted by the manufacturer and must be mounted by medical personal preoperatively or intraoperatively. The following paragraphs describe several optional configurations of cuffs that can be mounted easily to the catheter 12.

Figure 2:
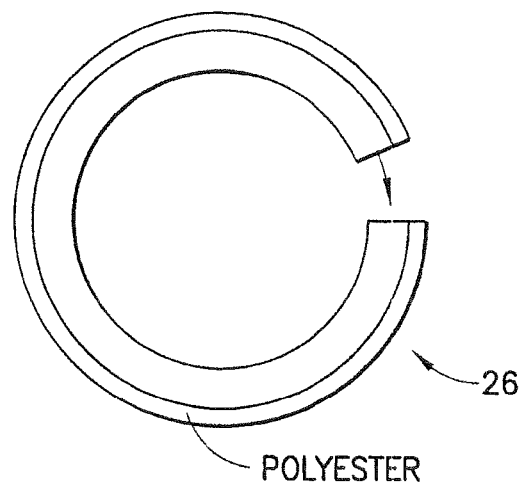
FIG. 2 is a schematic view of a cuff that can be used with the catheter of FIG. 1B.
Figure 3:
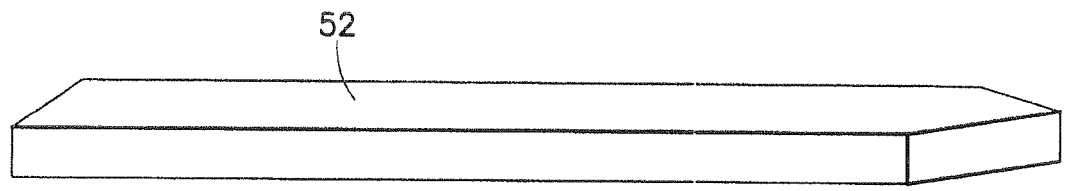
FIG. 3 is a perspective view of an outer belt of the cuff of FIG. 2.
Figure 4:
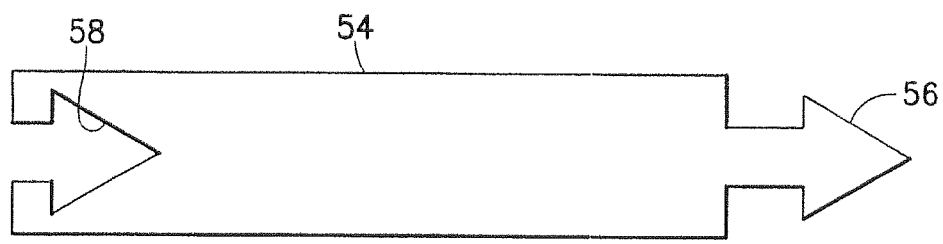
FIG. 4 is a top plan view of an inner belt for the top of FIG. 2.

One embodiment of the cuff 26 is illustrated in greater detail in FIGS. 2-4. The cuff 26 include a hollow outer belt 52 and an inner belt 54. The outer belt 52 preferably has polyester at least on the exterior. The interior of the hollow belt 52 preferably is formed to have a high friction surface. The inner belt 54 is configured to slide through the outer belt 52. The inner belt 54 has an arrow-shaped projection 56 on one end and a correspondingly configured recess 58 on the opposed end. Additionally, the inner belt 54 has a length that permits the projection 56 and the recess 58 to project slightly beyond the opposite ends of the outer belt 52. The inner belt 54 can be slid through the outer belt 52 by the manufacturer of the cuff 26 and can be configured as a ring by snapping the projection 56 into the recess 58. The assembled belts 52 and 54 thus are wrapped and secured around a portion of the tube 20 near the distal end 24.

Figure 5:
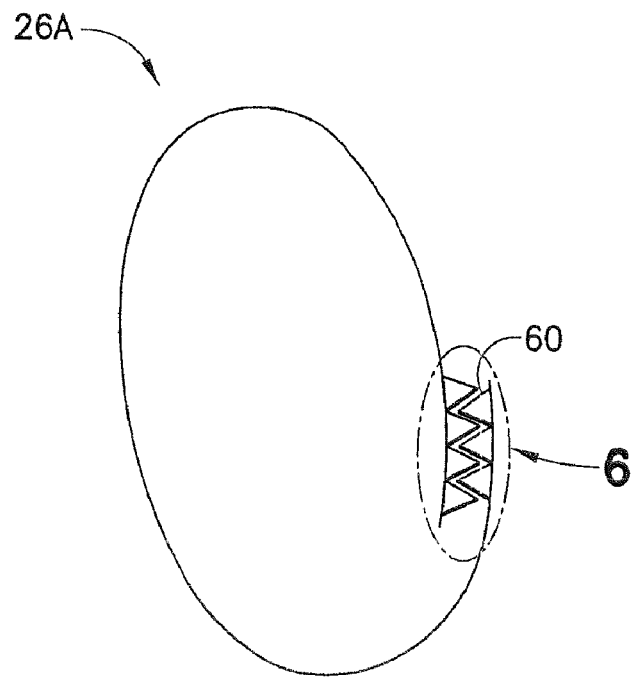
FIG. 5 is a schematic elevational view of a second embodiment of the cuff for the catheter of FIG. 1B.
Figure 6:
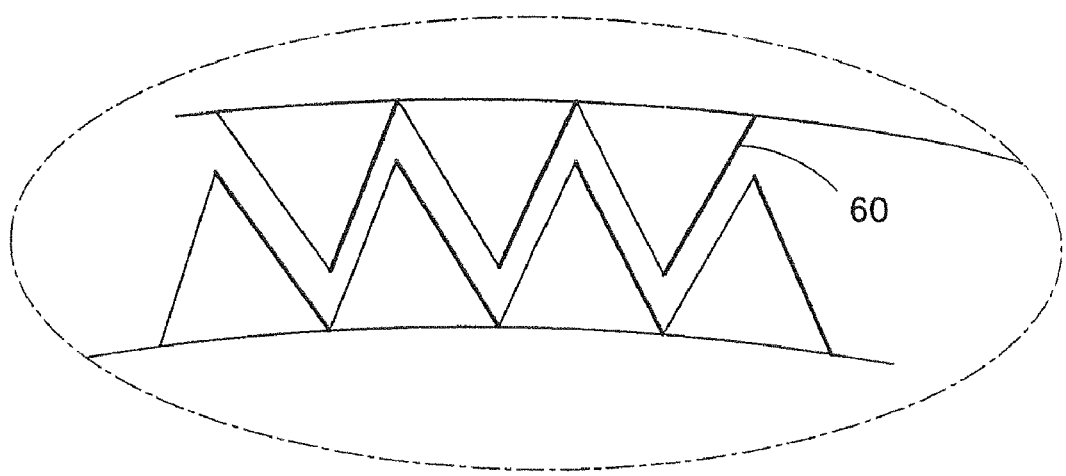
FIG. 6 is an enlarged schematic view of locked interengagement for the cuff of FIG. 5.

FIGS. 5 and 6 show an alternate cuff 26A. The cuff 26A is functionally similar to the cuff 26 illustrated in FIGS. 2-4. However, the cuff 26A includes interengagable teeth 60 that lock together when the cuff is flexed from the initial substantially linear condition into the annular condition. As in the embodiment of FIGS. 2-4, the cuff 26A of FIGS. 5 and 6 is dimensioned to securely engage on the tube 20. Additionally, both the cuff 26 and the cuff 26A may function to hold the tube 20 in position on the catheter 12.

A catheter in accordance with the second embodiment of the invention is identified by the numeral 62 in FIG. 7. The catheter 62 includes a proximal end 64 and a distal end 66. Portions of the catheter 62 adjacent the proximal end 64 are formed with non-cylindrical external surface configurations 68. In a preferred embodiment, as shown in FIG. 7, the exterior of the catheter 62 near the proximal end 64 includes an alternating arrangement of conical surfaces 68A intersecting radial surfaces 68B. Thus, a Christmas tree pattern is formed. The catheter 62 is used with a hub 70, as shown in FIG. 8. The hub 70 has a proximal end 72, a distal end 74 and a passage 76 extending therebetween. The passage 76 includes surface configurations that mate with the external surface configuration 68 near the proximal end 64 of the catheter 62. As a result, the proximal end 64 of the catheter 62 can be urged in a distal-to-proximal direction into the distal end 74 of the hub 70. This distal-to-proximal movement of the catheter 62 into the hub 70 is relatively easy. However, the radially aligned surfaces 68B of the Christmas tree configuration prevent the reverse movement, and hence prevent separation.

The hub 70 further includes tubular members 78 that can be connected with a dialysis machine. Additionally, the hub 70 includes the cuff 26 described above. The cuff 26 extends around the hub 70 for holding the hub 70 in secure engagement with the catheter 62. The catheter 62 and the hub 70 are used by trimming the proximal end 64 of the catheter 62 to an appropriate length and then inserting the trimmed proximal end 64 of the catheter in a distal-to-proximal direction into the open distal end 74 of the hub 70. The surface configurations 68 and 76 engage to prevent separation. The cuff 26 then is mounted around the hub 70 to hold the hub 70 and the catheter 62 together. Implantation proceeds as in the known art.

A third embodiment of a hub in accordance with the subject invention is identified generally by the numeral 80 in FIG. 9. The hub 80 has a proximal end 82, a distal end 84 and a passage 86 extending therethrough. A notch 88 is formed on the outer surface of the hub 80 near the distal end 84. A cuff 90, as shown in FIG. 10, can be pressed over the distal end 84 of the hub 80 and forcibly retained in the notch 88 to compress the hub 80 into engagement with the catheter 12. This assembly can be used substantially as with the previous embodiments and ensures that the distal end 16 of the catheter 12 can be positioned precisely and that the cuff 90 can be disposed at the preferred position for anchoring in the tunnel.

FIG. 11 shows a fourth embodiment with a catheter and hub assembly 92 that includes a catheter 94 with a proximal end 96 and a distal end 98. A plurality of arrays of external surface irregularities 100 are provided at spaced intervals on the catheter 94. Additionally a plurality of cuffs 102 are provided at spaced intervals on the catheter 94. The assembly 92 further includes a hub 104 that can be structurally similar to the hub 70 shown in FIG. 8. The catheter 94 can be trimmed to an appropriate length and the appropriate array of external surface regularities 100 then are inserted into locked engagement in the hub 104 substantially as described with respect to the embodiment of FIGS. 7 and 8.

A fifth embodiment of the subject invention is shown in FIGS. 12-15 and includes a catheter 110 with a proximal end 112 and a distal end 114. External surface regions of the catheter 110 extending distally from the proximal end 112 are formed with an array of external threads 116. A cuff ring 118 includes an array of internal threads 120 configured for threaded engagement with the threads 116 on the catheter 110, as shown in FIGS. 13 and 14. External surface areas of the cuff 118 include a polyester material that promotes growth of scar tissue for anchoring the catheter 110. The catheter 110 also is used with a hub 122. The hub 122 includes an array of internal threads 124 configured for mating with the external threads 116 on the catheter 110. The hub 122 further includes cannulas 126 that can engage in the lumen that pass through the catheter 110. The assembly shown in FIGS. 12-15 is used in a manner very similar to the embodiments depicted in FIGS. 1-11 and described above. In particular, portions of the catheter 110 adjacent the proximal end 112 are trimmed to an appropriate length that will achieve proper positioning of the distal end 114 of the catheter 110. The cuff 118 then is threaded onto the catheter 110 and is advanced from the trimmed proximal end 112 towards the distal end an appropriate amount for proper positioning of the cuff 118. The hub 122 then is threaded into engagement with the trimmed proximal end 112 of the catheter 110.

Figure 16:
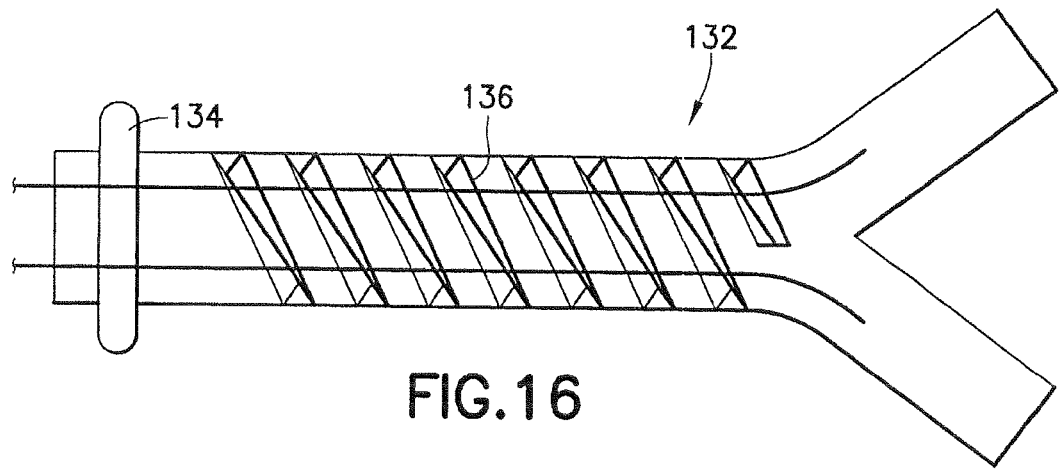
FIG. 16 is a schematic view of a hub in accordance with a sixth embodiment.

A variation of the embodiment shown in FIGS. 12-15 is depicted in FIG. 16. In particular, FIG. 16 shows a hub 132 with a cuff 134 permanently affixed thereto. The hub 132 has an array of internal threads 136 that can be threaded into engagement with the external threads 116 on the catheter 110 depicted in FIG. 12.

Figure 17:
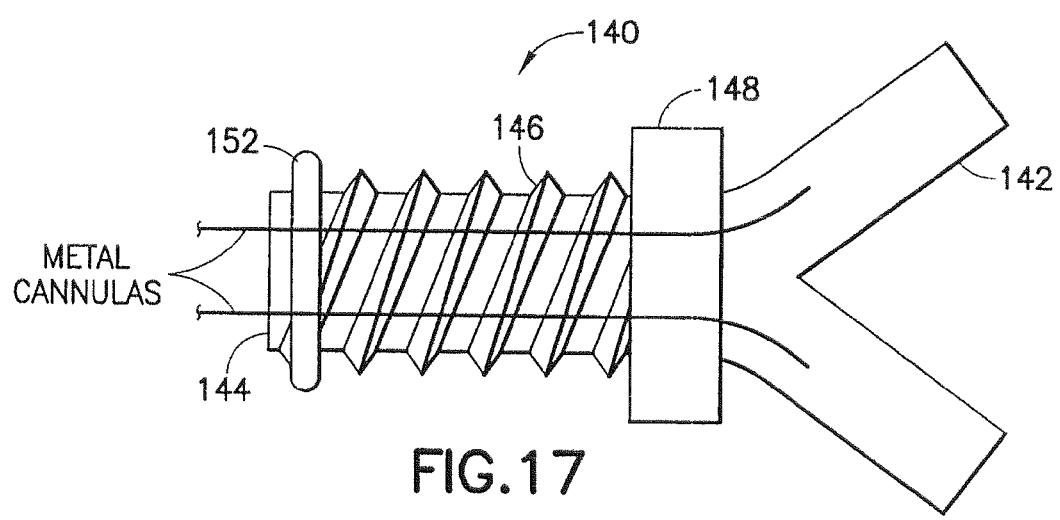
FIG. 17 is a schematic view of a hub in accordance with a seventh embodiment.

FIG. 17 shows a hub 140 that can be used with the catheter 12 described above and illustrated in FIG. 1. The hub 140 has a proximal end 142 and a distal end 144. Interior surface regions of the hub 140 are not threaded. However, the hub 140 includes an array of external threads 146. A cap or nut 148 is threadedly engaged with the external threads 146 on the hub 140. The nut 148 can be advanced in a proximal-to-distal direction and functions to tighten the hub 140 against the catheter 12 inserted therein. FIG. 17 shows a polyester cuff 152 mounted to the exterior of the hub 140 near the distal end 144. The mounting of the cuff 152 of the hub 140 can be by any of the above-described mounting means, including threaded engagement or snapped engagement into a groove or an arrangement where an initially linear cuff is wrapped around and locked into engagement around the hub.

Figure 18:
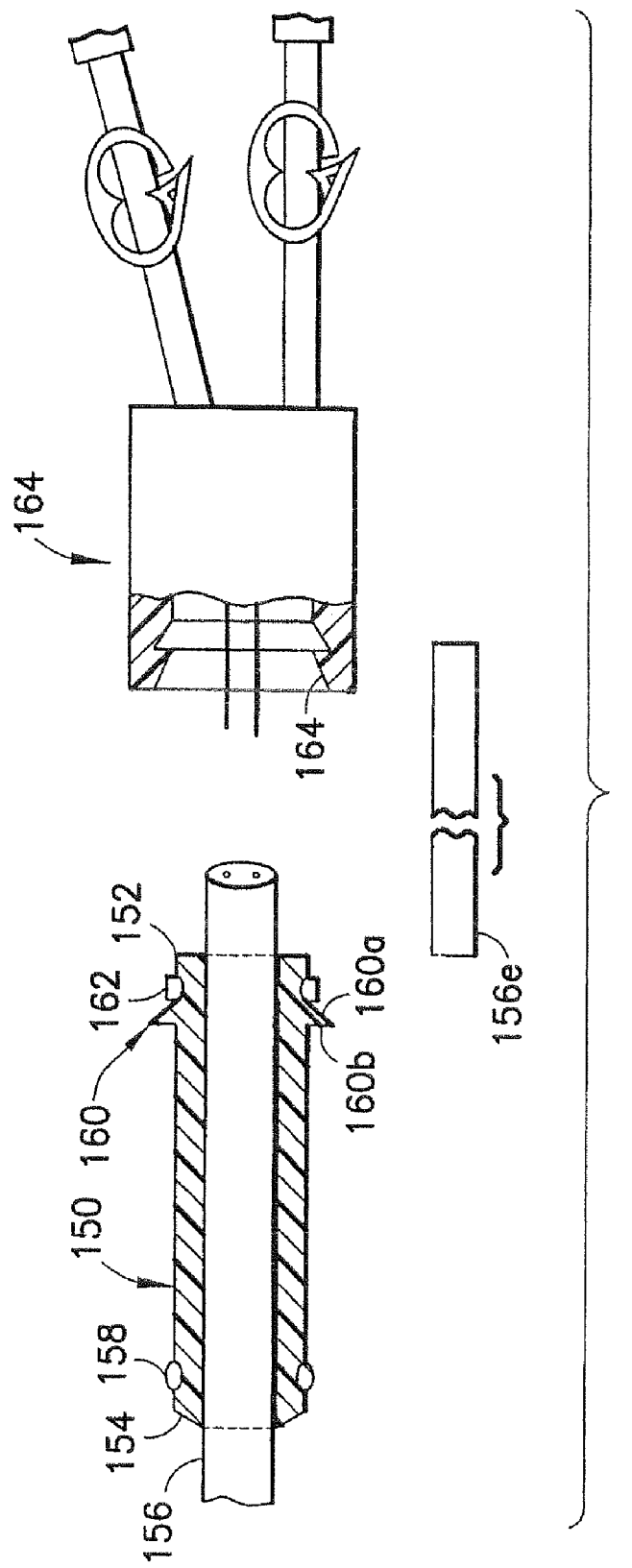
FIG. 18 is a schematic view of a cuff tube in accordance with an eighth embodiment.

FIG. 18 shows a further embodiment with a cuff tube 150 having a proximal end 152, and distal end 154 and a lumen extending between the ends. The lumen is configured for telescoping the cuff tube 150 over a catheter 156. The catheter 156 may be substantially identical to the catheter 12 described and illustrated with respect to the first embodiment. A cuff 158 is mounted around the cuff tube 150 near the distal end 154. In this regard, the cuff 158 can be mounted permanently to the cuff tube 150 with adhesive or the like applied by the manufacture of the cuff tube 150. Alternatively, any of the above described cuffs can be mounted to the cuff tube 150 by medical personal immediately prior to the deploying the cuff tube 150. With this latter option, the distal end 154 of the cuff tube 150 can be slit longitudinally so that the mounting of the cuff 158 thereon compresses the cuff tube 150 for at least partial retention of the cuff tube 150 on the catheter 156.

Hub attachments structures 160 are formed on the cuff tube 150 near the proximal end 152. In the illustrated embodiment, the hub attachment structure 160 is an annular rib with a sloped proximal face 160A and a radially aligned distal face 160B. A compression belt 162 is mounted around the cuff tube 150 near the proximal end 152 for squeezing proximal portions of the cuff tube 150 inwardly into the secure mechanical and fluid tight engagement with the catheter 156. Other attachments means can be employed in place of the compression belt 162, such as the known hose clamp for attaching a compressible hose to a nipple. In this regard, reference is made to the MSC Industrial Supply Co. catalog identified above and incorporated herein by reference.

The assembly of FIG. 18 further includes a hub 164. The hub 164 includes a distal end 166 with mounting structures 168 for securely engaging the hub 164 with the locking structure 160 on the cuff tube 150. The catheter assembly shown in FIG. 18 is employed by utilizing a catheter 156 that is assured to have at least the maximum required length. The catheter 156 is inserted so that the distal end of the catheter 156 is properly positioned in the patient and so that the proximal end of the catheter 156 extends from patient. The cuff tube 150 then is telescoped over the catheter 156 so that the cuff 158 is at a desired position for anchoring in the patient by scar tissue that will grow around the cuff 158. The compression belt 162 or other attachment means then is tightened on or near the proximal end 152 of the cuff tube 150. A proximal excess portion 156e of the catheter 156 then is trimmed at or near the proximal end 152 of the cuff tube 150. The hub 164 then is telescoped over the proximal end 152 of the cuff tube 150. As a result, the attachment structures 168 near the distal end 166 of the hub 164 securely engage the attachment structures 160 on the cuff tube 150.

The configurations of the cuff tube and the hub can vary from those shown in FIG. 18. For example, FIG. 19 shows a cuff tube 150a formed from a hard plastic and having proximal end 152a, a distal end 154a and lumen 156a extending between the ends. A polyester cuff 158a or other fibrosing agent is mounted around the cuff tube 150a near the distal end 154a. The lumen 156a includes a tapered entry 160a adjacent the proximal end 152a. Additionally, an annular locking groove 162a is formed immediately adjacent to and distally of the tapered entry 160a. The cuff tube 150a is used with a hub assembly 164a that is structurally and functionally similar to the hub assembly 50 described above with respect to FIG. 1. However, the hub assembly 164a is formed from a material that is softer and/or thinner than the hard plastic of the cuff tube 150a. Hence, the hub assembly 164a is more readily compressible than the cuff tube 150a. The hub assembly 164a includes a distal end 166a and a conically tapered portion 168a adjacent the distal end 166a. The conically tapered portion 168a flares outwardly to greater cross sections at distances further from the distal end 166a. The catheter 169a is inserted through the tube 150a and trimmed to a preferred length, as described above. The excess of the catheter then is discarded, and the hub 164a is inserted into the cuff tube 150a. The tapered shape the surface 168a on the hub assembly 164a and the tapered entry 160a at the proximal end 152a of the cuff tube 150a are substantially complementary. As a result, and in view of the thinner/softer material of the hub 164a, portions of the hub assembly 164a near the distal end 166a will be compressed inwardly into secure engagement with the catheter 169a. The large diameter end of the tapered portion 168a will be engaged in the locking groove 162a. This variation will avoid the need to employ a separate compressive belt or other such attachment means for securing the cuff tube to the catheter.

A further variation of the catheter assembly of the subject invention is illustrated in FIG. 20. This embodiment employs a conventional catheter 12 comparable to the catheter shown in FIG. 1. A C-shaped cuff 170 is mounted on a slit cylindrical cuff positioning tube 172. In this embodiment, the catheter 12 is positioned as described above. The slit tube 172 is mounted over the catheter 12 and is moved distally along the catheter 12 in the direction of arrow A until the cuff 170 is an appropriate position. The tube 172 then is snapped together by securing opposed longitudinal edges of the slit tube 172 together. Inner circumferential surfaces of the tube may be coated or lined with a material that will ensure fluid tight fit of the tube 172 to the catheter 12. The catheter 12 can be trimmed at the proximal end and a hub can be mounted as in other embodiments.

Figure 21:
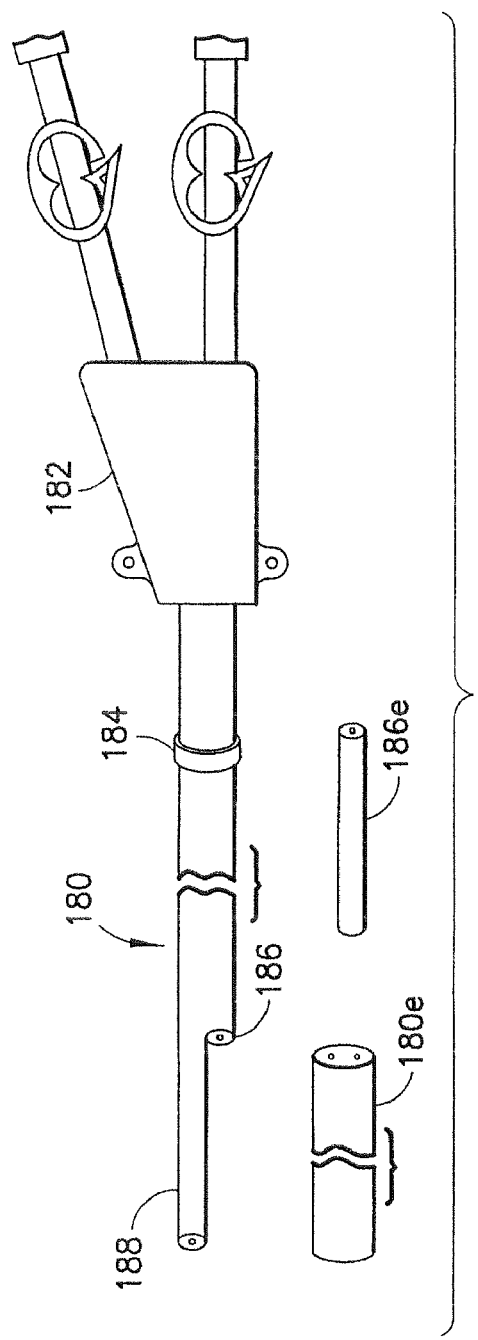
FIG. 21 is a schematic view of an eleventh embodiment with a distally trimmable catheter.

FIG. 21 as shows another variation of the assembly for assuring accurate positioning of the tip of the catheter. In this regard, the catheter 180 is provided with a length that exceeds the maximum anticipated length. A hub assembly 182 is provided at proximal end of the catheter 180 and a cuff 184 is mounted in slightly spaced relationship to the hub assembly 182. Distal portions of the catheter 180 are cut to achieve an appropriate length, and the extreme distal end 180e that is cut from the catheter 180 then is discarded. One lumen 186 of the catheter 180 is cut in a distal position and the excess 186e is discarded so that the lumen 186 is shorter than the catheter 188. The tube lumen then may be separated from one another. The catheter 180 can be inserted in a conventional manner and ensures proper positioning of both distal and proximal ends of the catheter relative to the patient without maintaining a complicated inventory of parts.

Figure 22:
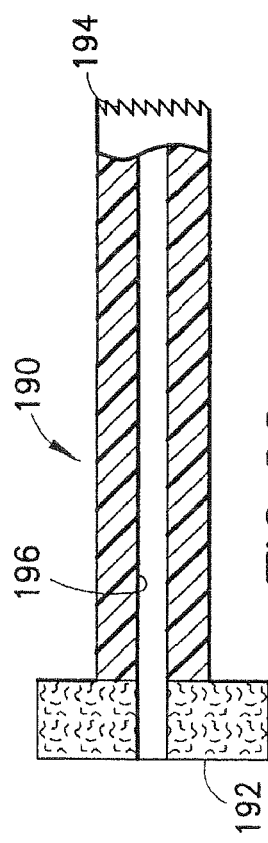
FIG. 22 is a schematic view of a tool for separating the cuff from scar tissue.

Catheter assemblies may require removal. As noted above, prior art catheters have required a complicated dissection of the cuff from the patient. The catheter assembly of the subject invention, however, may be used with a cuff removal tool 190, as shown in FIG. 22. In particular, the cuff removal tool 190 is a generally slit tubular structure with a proximal end 192 and a distal end 194. The proximal end 192 is configured to define a handle and is roughened or knurled to facilitate manipulation and turning of the tool 190. The distal end 194 defines an array of sharp cutting teeth. The tool 190 is used by telescoping the proximal end 194 of the tube 190 over the catheter. This mounting of the tool 190 over the catheter can be achieved by transversally moving portions of the catheter through the slit 196 defined in the tube 190. The tool 190 then is rotated so that the teeth cut the scar tissue. Thus the catheter can be removed easily.

Figure 23:
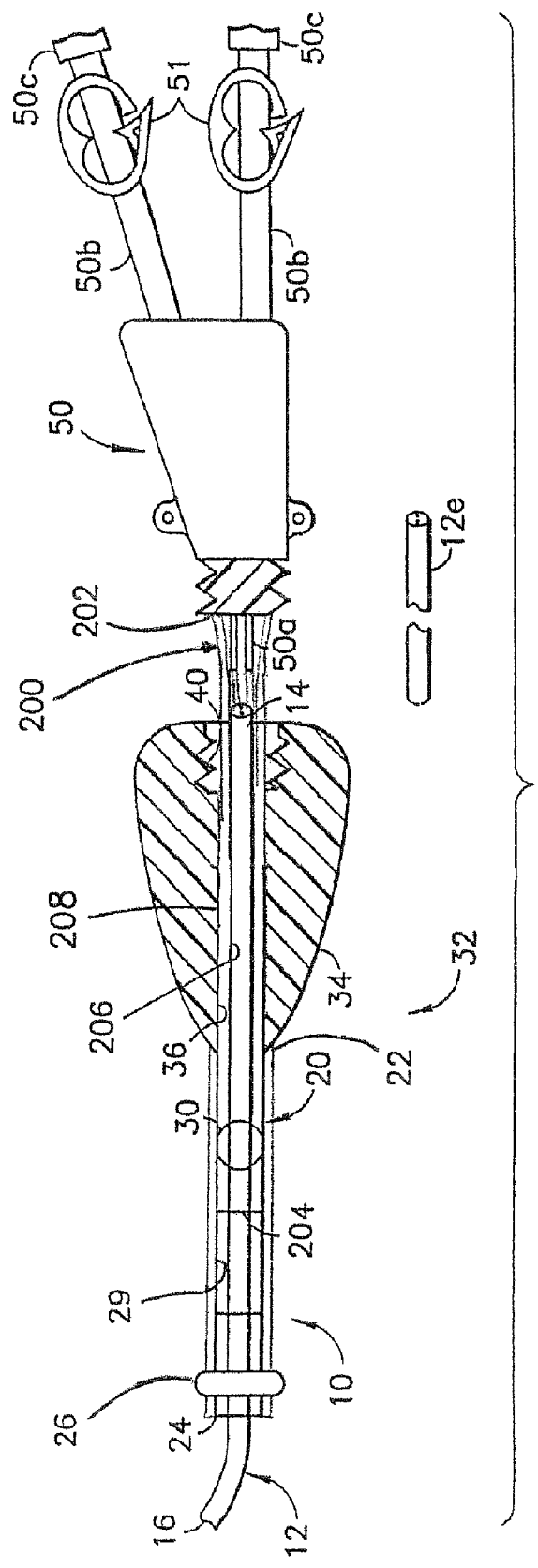
FIG. 23 is a schematic view of a twelfth embodiment in an exploded condition.
Figure 24:
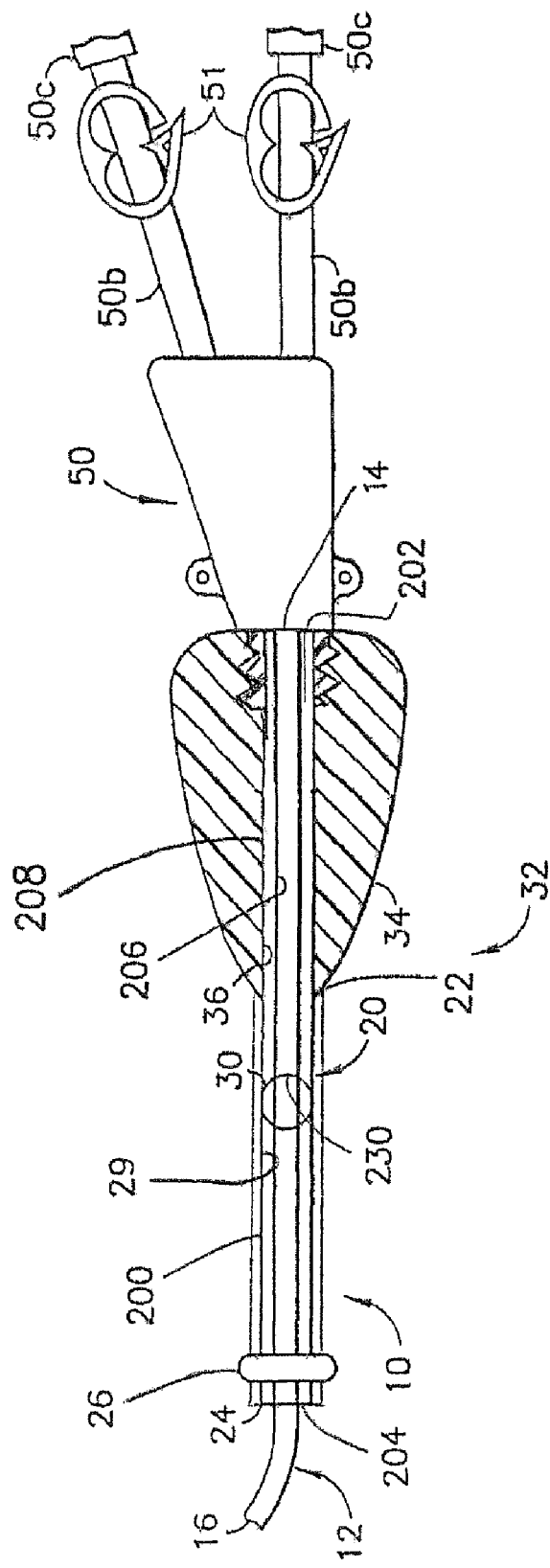
FIG. 24 is a schematic view of the twelfth embodiment in a full assembled condition.

FIGS. 23 and 24 show an embodiment of the invention similar to the embodiment shown in FIG. 1A. More particularly, the embodiment of FIGS. 23 and 24 is used with a catheter 12 substantially identical to the catheter 12 of the embodiment shown in FIG. 1A. The catheter 12 includes a proximal end 14, a distal end 16 and lumens extending between the ends. The embodiment of FIGS. 23 and 24 further includes a hub assembly 50 that is substantially identical to the hub assembly of the embodiment shown in FIG. 1A. However, the metal cannulas 50a of the hub 50 project farther in the distal direction in the embodiment of FIGS. 23 and 24. Still further, the embodiment of FIGS. 23 and 24 includes an outer subcutaneous tube 20 that is substantially the same as the subcutaneous tube 20 of the embodiment shown in FIG. 1A. In this regard, the outer subcutaneous tube 20 has a proximal end 22, a distal end 24 and a lumen 29 extending between the ends. A polyester cuff 26 or other fibrosing agent is disposed around the outer circumferential surface of the outer subcutaneous tube 20 at locations near the distal end 24. A cap 34 has a distal end mounted permanently to the proximal end 22 of the outer subcutaneous tube 20 so that the cap 34 and the outer subcutaneous tube 20 define an integral subassembly. The cap 34 also has a proximal end and a lumen 36 extending between the ends. Portions of the lumen 36 at the proximal end of the cap 34 have threads 40 for threadedly engaging threads on the hub 50.

Unlike the embodiment of FIG. 1A, the embodiment of FIGS. 23 and 24 further includes an inner subcutaneous tube 200. The inner subcutaneous tube 200 has a proximal end 202, a distal end 204 and a lumen 206 extending between the ends. The lumen 206 of the inner subcutaneous tube 200 is configured and dimensioned so that the proximal end 14 of the catheter 12 can be inserted into the lumen 206 of the inner subcutaneous tube 200. The inner subcutaneous tube 200 has an outer circumferential surface 208 that is dimensioned cross-sectionally to be received slidably in the lumen of the outer subcutaneous tube 20. In this regard, portions of the lumen of the outer subcutaneous tube 20 preferably are reduced to a slightly smaller inside diameter at the distal end 24 to press the inner subcutaneous tube inwardly for achieving close engagement between the outer subcutaneous tube 20, the inner subcutaneous tube 200 and the catheter 12 and for preventing fluid flow between these three tubular members. Portions of the inner subcutaneous tube 200 adjacent the proximal end 202 preferably are flared outwardly slightly and are engaged permanently with the hub 50 so that the hub 50 and the inner subcutaneous tube 200 define an integral subassembly. The inner subcutaneous tube 200 also has a transparent window 230 registered with the window 30 in the outer subcutaneous tube 20 to permit observation of the catheter 12 for accurately gauging the volume of heparin solution that should be inserted into the assembly. The metal cannulas 50a that extend from the hub 50 are dimensioned in this embodiment to project to the distal end 204 of the inner subcutaneous tube 200.

The embodiment of the invention depicted in FIGS. 23 and 24 is used by first inserting the distal end 16 of the catheter 12 into the patient in a conventional manner. The insertion of the catheter 12 can be performed in an antegrade or retrograde manner. Portions of the catheter 12 adjacent the proximal end 14 are trimmed to a length appropriate for the patient.

The physician then accesses an assembly that comprises the integral subassembly of the hub 50 and the inner subcutaneous tube 200 loosely engaged with the integral subassembly of the cap 34 and the outer subcutaneous tube 20. More particularly, the hub 50 is assembled permanently (e.g. adhered or welded) with the inner subcutaneous tube 200 by the manufacturer. Similarly, the cap 34 is assembled permanently (e.g. adhered or welded) to the outer subcutaneous tube 20 by the manufacturer. Additionally, the outer and inner subcutaneous tubes 20 and 200 are telescoped together by the manufacturer and the threads 40 of the cap 34 are loosely engaged with the threads of the hub 50. The trimmed proximal end 14 of the catheter 12 then is inserted into the distal end 204 of the inner subcutaneous tube 200 and into communication with the metal cannulas 50a of the hub 50. The hub 50 and the cap 34 then are tightened threadedly relative to one another to achieve the connected state shown in FIG. 24. As a result, the cap 34 squeezes the proximal end 202 of the inner subcutaneous tube 200 and deforms the inner subcutaneous tube 200 inwardly for securely holding the catheter 12 in the lumen 206 of the inner subcutaneous tube 200 and for achieving a fluid-tight seal between the inner subcutaneous tube 200 and the catheter 12. This assembly then is advanced distally so that the distal end 24 of the outer subcutaneous tube 20 advances into the subcutaneous tunnel prepared in the patient and so that the fibrous cuff 26 reaches a position for secure anchoring in the patient due to tissue ingrowth into the cuff 26.

A dialysis catheter occasionally must be replaced due to infection or blockage. In the prior art, the entire assembly would have to be removed, and this procedure would require separating the fiber cuff from the tissue of the patient that had grown into the fiber cuff. This is a somewhat complicated and invasive procedure. However, the embodiment of the invention depicted in FIGS. 23 and 24 avoids the complications associated with any required exchange of the catheter. More particularly, the catheter 12 of FIGS. 23 and 24 can be replaced merely by unthreading the hub 50 from the cap 34 at the proximal end of the outer subcutaneous tube 20. The integral subassembly of the hub 50 and the inner subcutaneous tube 200 then merely is removed from the patient without dislodging the outer subcutaneous tube 20. The catheter 12 then is removed without dislodging the outer subcutaneous tube 20. A new catheter 12 then is inserted through the lumen of the outer subcutaneous tube 20 and at least partly towards it final position in the blood vessel of the patient. The proximal end 14 of the new catheter 12 then is trimmed to an appropriate length. The trimmed proximal end 14 of the replacement catheter 12 then is placed in communication with a new subassembly that comprises a new subcutaneous tube 200 and a new hub 50. The new catheter 12, the new inner subcutaneous tube 200 and the hub 50 then are advanced distally to the final position in the patient and are tightened into the cap 34 at the proximal end 22 of the previously anchored outer subcutaneous tube 20.

The embodiment of the invention depicted in FIGS. 23 and 24 has the advantages described with respect to the previous embodiments as well as additional advantages. In this regard, the embodiment of the invention depicted in FIGS. 23 and 24 enables a precise control for the positioning both the tip at the distal end of the catheter 12 and cuff 26 on the outer subcutaneous tube 20. As in the prior embodiments, the embodiment of the invention depicted in FIGS. 23 and 24 avoids the need for a large inventory of catheters 12 of different lengths that must be selected in view of the size of the patient. The embodiment of the invention depicted in FIGS. 23 and 24 also is well suited for both antegrade and retrograde insertion of the catheter 12 in the patient. Furthermore, the embodiment of the invention depicted in FIGS. 23 and 24 permits an easy exchange of a catheter 12 that has become infected or blocked. The use of inner and outer subcutaneous tubes 20 and 200, as depicted in FIGS. 23 and 24, also is very effective at protecting the catheter 12 from ascending infection. Still further, the illustrated use of two subcutaneous tubes 20, 200 is effective at preventing bleeding at the exit site of the subcutaneous tunnel. Additionally, and importantly, the outer subcutaneous tube 20 has an inside diameter that exceed the outside diameter of the catheter 12 by the radial thickness of the inner subcutaneous tube 200. Thus, the outer subcutaneous tube 20 will not scrape off the fibrin sheath that accumulates on the outer surface of the catheter 12, and the catheter 12 can be removed without producing debris that might otherwise remain in the patient.

Any of the above-described cuffs or variations thereof may comprise or consist of a fibrosing agent. Known fibrosing agents include, but are not limited to silk, collagen, talc, talcum powder, beryllium, copper, silica, quartz, EVA, PLA, polyurethanes and polymerized drug compositions. A discussion of fibrosing agents is provided in published U.S. Patent Appl. Pub. No. 2005/0191248 the disclosure of which is incorporated herein by reference.

What is claimed is:

1. A dialysis catheter assembly comprising:
   a subcutaneous tube for semi-permanent retention in a patient;
   fibrosing means on the subcutaneous tube for promoting a growth of scar tissue for anchoring the subcutaneous tube in the patient; and
   a removal tool for selectively cutting the scar tissue to enable removal of the subcutaneous tube, the removal tool having a substantially tubular structure with a substantially uniform internal diameter dimensioned to telescope over the subcutaneous tube, a substantially uniform external diameter, a proximal end, a distal end and a slit through the tubular structure from the proximal end to the distal end, the substantially tubular structure having first and second opposed edges facing one another at opposite sides of the slit, the substantially tubular structure being circumferentially continuous from the first edge to the second edge in a circumferential direction extending circumferentially away from the slit, a handle positioned at the proximal end of the tubular structure, said handle being configured to facilitate manipulation and turning of the tool, and a cutting edge at the distal end of the tubular structure and including a substantially circular array of distally-pointing, sharp cutting teeth.

2. The dialysis catheter assembly of claim 1, wherein the slit has a width that enables the subcutaneous tube to be urged through the slit and into the tubular structure.

3. The dialysis catheter assembly of claim 1, wherein the handle projects radially out from the subcutaneous tube.

* * * * *